United States Patent
Tsujii (10) Patent No.: US 7,277,525 B2
(45) Date of Patent: Oct. 2, 2007

(54) RADIOGRAPHIC DEVICE AND RADIOGRAPHIC METHOD

(75) Inventor: Osamu Tsujii, Utsunomiya (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 11/489,088

(22) Filed: Jul. 19, 2006

(65) Prior Publication Data
US 2006/0256920 A1    Nov. 16, 2006

Related U.S. Application Data

(63) Continuation of application No. PCT/JP05/00789, filed on Jan. 21, 2005.

(30) Foreign Application Priority Data

Jan. 22, 2004    (JP)    ............................. 2004-013835

(51) Int. Cl.
*A61B 6/03*    (2006.01)
(52) U.S. Cl. ...................... 378/19; 378/98.7
(58) Field of Classification Search .................... 378/4, 378/15, 19, 114, 98.7
See application file for complete search history.

(56) References Cited

U.S. PATENT DOCUMENTS 6,018,563 A * 1/2000 Arai et al. .................. 378/98.7
6,148,058 A * 11/2000 Dobbs .......................... 378/19
6,865,248 B1 * 3/2005 Rasche et al. ................. 378/4

FOREIGN PATENT DOCUMENTS

| JP | 07-124152 | 5/1995 |
| JP | 08-206107 | 8/1996 |
| JP | 09-288184 | 11/1997 |
| JP | 10-021372 | 1/1998 |
| JP | 10-225454 | 8/1998 |
| JP | 2000-0217810 | 8/2000 |
| JP | 2001-231779 | 8/2001 |

* cited by examiner

*Primary Examiner*—Chih-Cheng Glen Kao
(74) *Attorney, Agent, or Firm*—Cowan, Liebowitz & Latman, P.C.

(57) ABSTRACT

An object is rotated by a rotation device 15 in X rays 25 generated by a X-ray generation device 11. The rotation device 15 makes constant the integration value of the X rays 25 reaching a two-dimensional X-ray sensor 12 during each charge integration time during which a plurality of image data are acquired.

9 Claims, 10 Drawing Sheets

RADIOGRAPHIC DEVICE AND RADIOGRAPHIC METHOD

CROSS-REFERENCE TO RELATED APPLICATIONS

This application is a continuation of International application Ser. No. PCT/JP/2005/000789, filed Jan. 21, 2005, which is based on Japanese Patent Application No. 2004-013835, filed on Jan. 22, 2004.

TECHNICAL FIELD

The present invention relates to a radiographic device that generates an image on the basis of X-ray image data obtained by performing a radiographic operation while rotating an object relative to X rays, and in particular, to a technique for suitably controlling the speed at which the object is rotated.

BACKGROUND ART

In recent years, much effort has been made to develop two-dimensional X-ray sensors (also referred to as "FPDs (Flat Panel Detectors)) for radiography in order to acquire digital data for large screens (see Patent Document 1: Japanese Patent Laid-Open No. 09-288184). A radiographic device has been applied to medical radiography; the radiographic device performs a plain radiographic operation using a two-dimensional X-ray sensor having a large detector surface of size 43×43 cm.

On the other hand, another radiographic device is known which exposes the object to X rays and uses an X-ray detector to detect the dose of X-ray radiation having penetrated the object, thus obtaining projection image data (sometimes called "scanogram" or "SCOUT image"), tomogram, or three-dimensional image data on the object on the basis of the X-ray detection output (photon count of the X ray) from the X-ray detector.

An improvement in a technique for developing a two-dimensional X-ray sensor has resulted in development of a cone beam CT (Computed Tomography) device (hereinafter referred to as a CBCT device) that is a radiographic device that generates three-dimensional image data. Conventional X-ray CT devices use X-ray beams that are sliced thin in a Z direction (body axis direction); these X-ray beams are called fan beams. In contrast, the CBCT device uses X-ray beams spreading also in the Z direction (hereinafter referred to as "cone beams") and receives the cone beams using a two-dimensional detector (having a built-in two-dimensional X-ray sensor). Compared to the CT device using fan beams, the CT device using cone beams can image a wider range of the object during one rotation of scan. This reduces the number of rotations required for computed tomography, thus advantageously allowing a radiographic operation to be efficiently performed. In other words, a radiographic operation can be efficiently performed by increasing a cone angle (spread angle in the Z direction) corresponding to the spread of cone beams. On the other hand, too large a cone angle disadvantageously results in an error in image generation.

A certain type of cone beam CT device (hereinafter referred to as a CBCT device) carries out scanning (collects image data) while rotating a pair of an X-ray source and a detector around the object as shown in Patent Document 2 (Japanese Patent Laid-Open No. 10-21372) (image data may be referred to as "projection images"). However, to irradiate the entirety of the large detector surface of a two-dimensional detector with radiation from a radiation source, having a cone angle less than a given angle, at least a given distance must be set between the two-dimensional detector and the radiation source. Accordingly, with a CBCT device of a type that carries out scanning (collects image data) while rotating a pair of an X-ray source (X-ray generation device) and a detector around the object, it is very difficult, owing to the size of the device, to set a certain distance between the two-dimensional detector and the radiation source so as to allow the large detector surface of the two-dimensional detector to be effectively used.

On the other hand, effort has been made to develop and put to practical use an object rotating type CBCT device that rotates the object while a pair of an X-ray source and a two-dimensional detector has been fixed as described in Patent Document 3 (Japanese Patent Laid-Open No. 2000-217810). The object rotating type CBCT device acquires image data at every given rotation angle and uses a plurality of acquired image data to reconstruct an image.

The penetration rate of X rays varies depending on the direction in which the X rays are incident on the human body. Further, to obtain a predetermined image SN ratio, it is necessary that X-ray radiation of at least a given dose reaches the two-dimensional detector. Moreover, the dose of X-ray radiation to which the patient is exposed needs to be minimized. Thus, the dose of X-ray radiation reaching the two-dimensional detector during acquisition of one image data desirably falls within a predetermined range.

The following is used to solve the above problems, in a spiral CT and a multi-slice CT which are the traditional type of X-ray CT device rotating the X-ray source: (1) a method of adjusting X rays emanated by the X-ray generating means, for each slice position on the basis of projection image data or (2) a method of adjusting X rays emanated by the X-ray source, at every rotation angle on the basis of data on the dose of X-ray radiation having penetrated the patient. In other words, the conventional CT devices adjust the dose of X-ray radiation reaching the detector (sensor unit) by adjusting the output from the X-ray generation device (Patent Document 4 (Japanese Patent Laid-Open No. 07-124152) and Patent Document 5 (Japanese Patent Laid-Open No. 08-206107)).

On the other hand, the object rotating type CBCT device can be used as a radiographic device for normal plain radiography by stopping the rotation of the object (testing object). That is to say, the single device can advantageously be used both for CT and for plain radiography. Further, it has been proposed that X-ray generation devices for plain radiography already installed in general hospitals be diverted to object rotating type radiographic devices. Moreover, it has been desired that a single X-ray generation device be used both as a radiographic device for plain radiography and as an object rotating type radiographic device.

DISCLOSURE OF THE INVENTION

Problems to be Solved by the Invention

With the techniques described in Patent Documents 4 and 5, a computer controls the X-ray generation device on the basis of penetration data from a particular object to adjust X-ray outputs, that is, the reaching dose of X-ray radiation. However, if an X-ray generation device for plain radiography already installed in a general hospital is used as an object rotating type radiographic device, it is difficult to control the output from the X-ray generation device in association with rotation of a rotating mechanism. In general, the X-ray generation device is not adapted to control X-ray outputs in liaison with an external system.

Through wholehearted relevant studies, the present inventor has found that in connection with development of an object rotating type X-ray CT device, it is difficult to allow an X-ray generation device to operate in liaison with a rotation device that rotates the object and control the dose of X-ray radiation reaching a two-dimensional X-ray sensor to a predetermined value.

An object of the present invention is thus to provide a radiographic device that executes an imaging process while rotating an object relative to X rays, the radiographic device allowing the dose of X-ray radiation reaching an X-ray sensor in each radiographic process to be controlled to a predetermined value without the use of an X-ray generation device whose outputs can be externally adjusted.

MEANS FOR SOLVING THE PROBLEMS

A radiographic device provided according to an aspect of the present invention to achieve the above object is organized as described below. The radiographic device comprises:

X-ray generation means for generating X rays;

rotation means having a rotation mechanism that relatively rotates an object in a region irradiated with the X rays; and an X-ray sensor that executes a plurality of imaging processes using X rays having penetrated the object while the object is being rotated by the rotation means, to acquire a plurality of first image data, wherein the rotation means controls a rotation speed of the rotation mechanism so that the X rays reaching the X-ray sensor during a charge integration time in each of the plurality of imaging processes have a fixed integration value during rotation of the rotation mechanism.

A radiographic method provided according to another aspect of the present invention to achieve the above object comprises:

an X-ray generation step of generating X rays by X-ray generation means;

a rotation step of rotating a rotation mechanism that relatively rotates an object in a region irradiated with the X rays; and an imaging step of executing a plurality of imaging processes using X rays having penetrated the object during rotation of the object by the rotation step, to acquire a plurality of first image data, wherein, in the rotation step, a rotation speed of the rotation mechanism is controlled so that the X rays reaching the X-ray sensor during a charge integration time in each of the plurality of imaging processes have a fixed integration value during rotation of the rotation mechanism.

ADVANTAGES OF THE INVENTION

The present invention provides a radiographic device that executes an imaging process while rotating an object relative to X rays, which allows the dose of X-ray radiation reaching an X-ray sensor in each radiographic process to be controlled to a predetermined value without the use of an X-ray generation device allowing its outputs to be externally adjusted.

The other features and advantages of the present invention will be apparent from the description below taken in conjunction with the accompanying drawings.

BRIEF DESCRIPTION OF DRAWINGS

The accompanying drawings incorporated into and constituting a part of the present specification illustrate embodiments of the present invention and clarify the principle of the present invention in conjunction with the description below.

BEST MODE FOR CARRYING OUT THE INVENTION

Preferred embodiments of the present invention will be described below in detail with reference to the accompanying drawings (FIGS. 1 to 6).

FIRST EMBODIMENT

Figure 1:
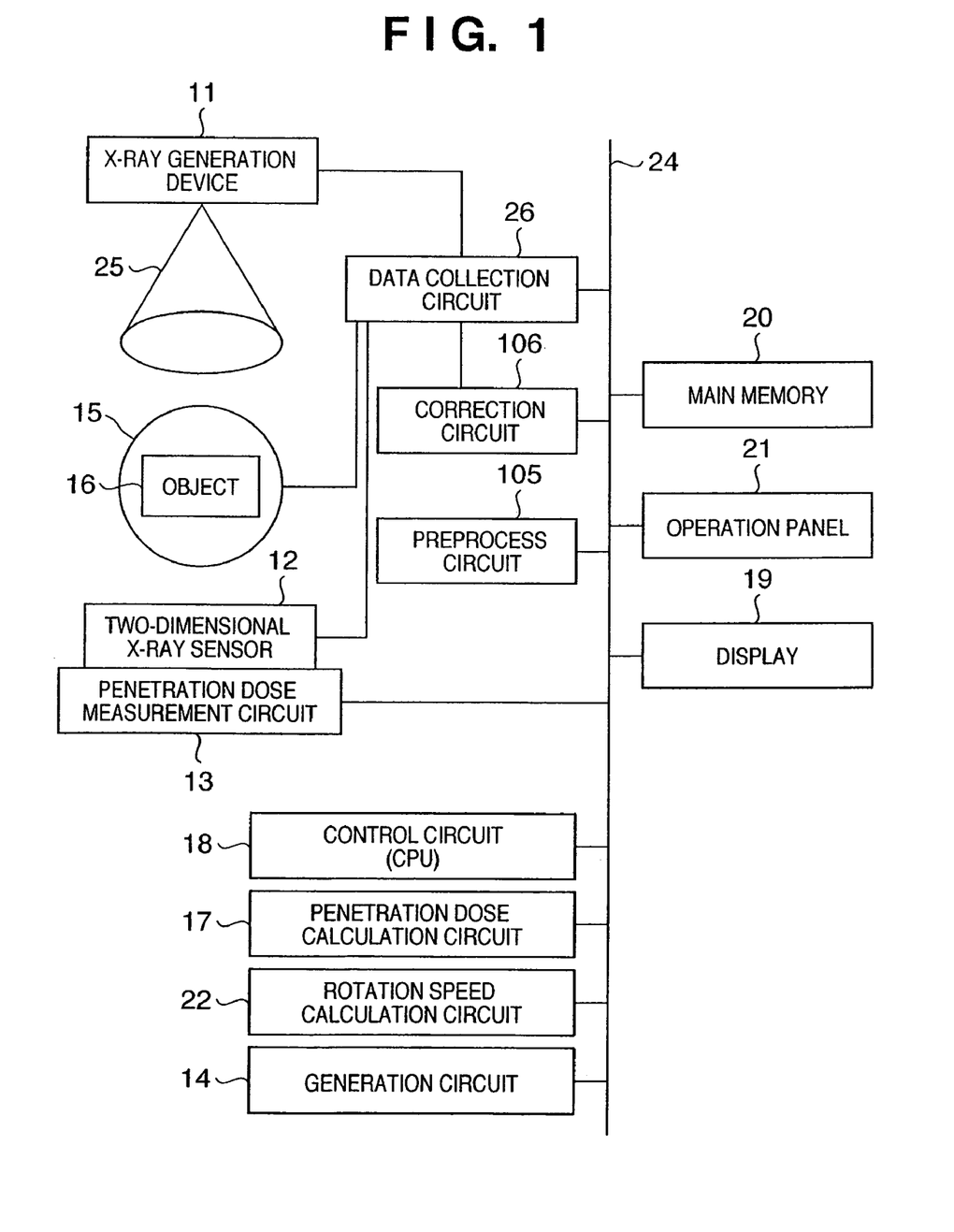
FIG. 1 is a diagram showing an example of general organization of a radiographic device according to an embodiment.
Figure 2:
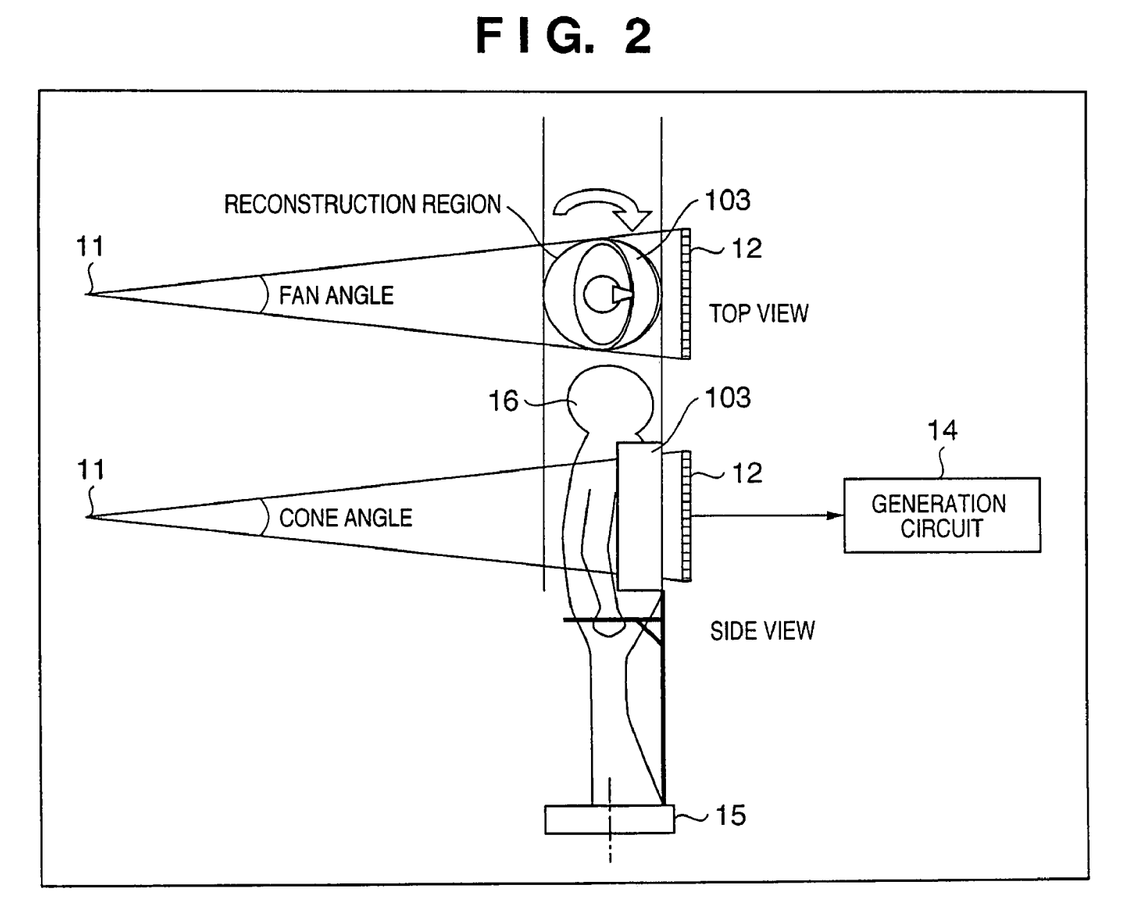
FIG. 2 is a diagram showing an example of arrangement of an object rotating type radiographic device.
Figure 3:
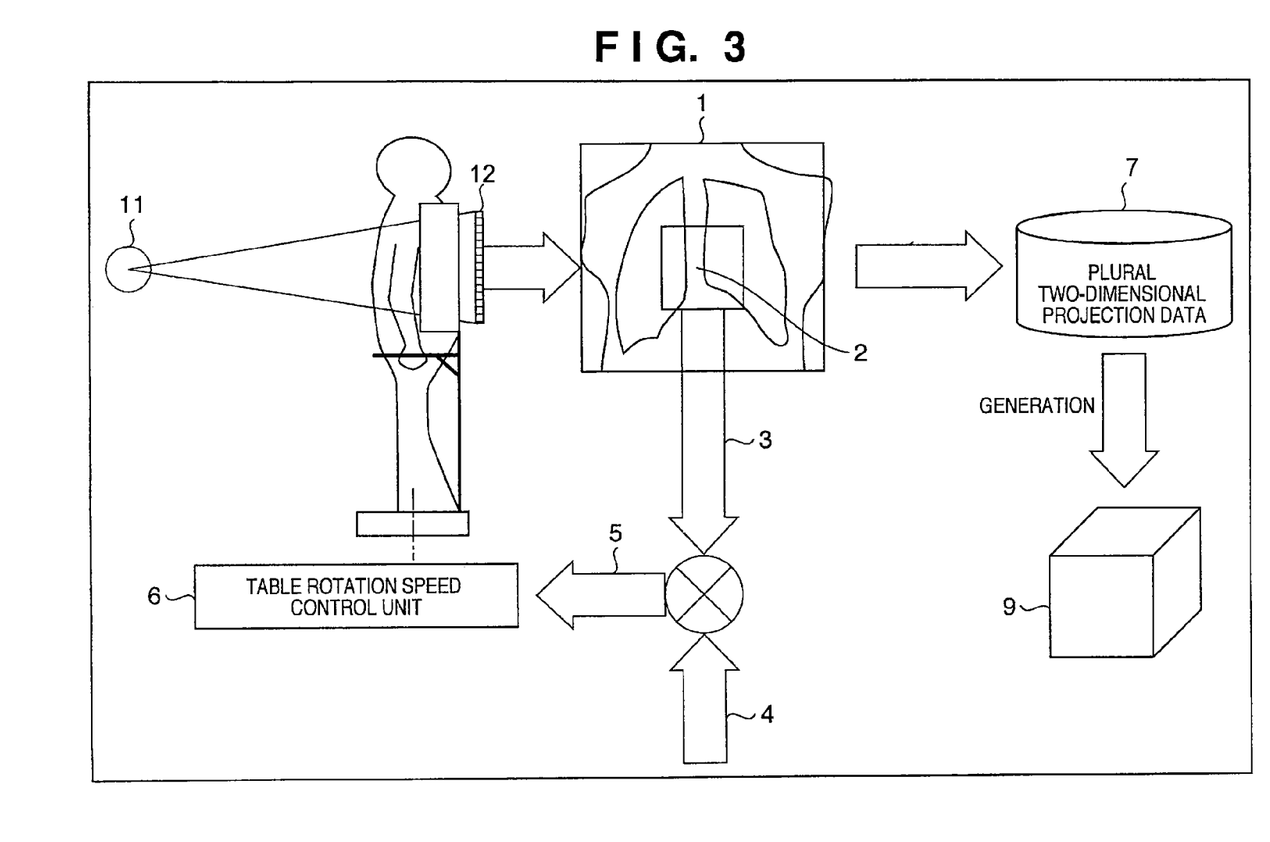
FIG. 3 is a conceptual drawing schematically illustrating an imaging process according to a first embodiment.
Figure 4:
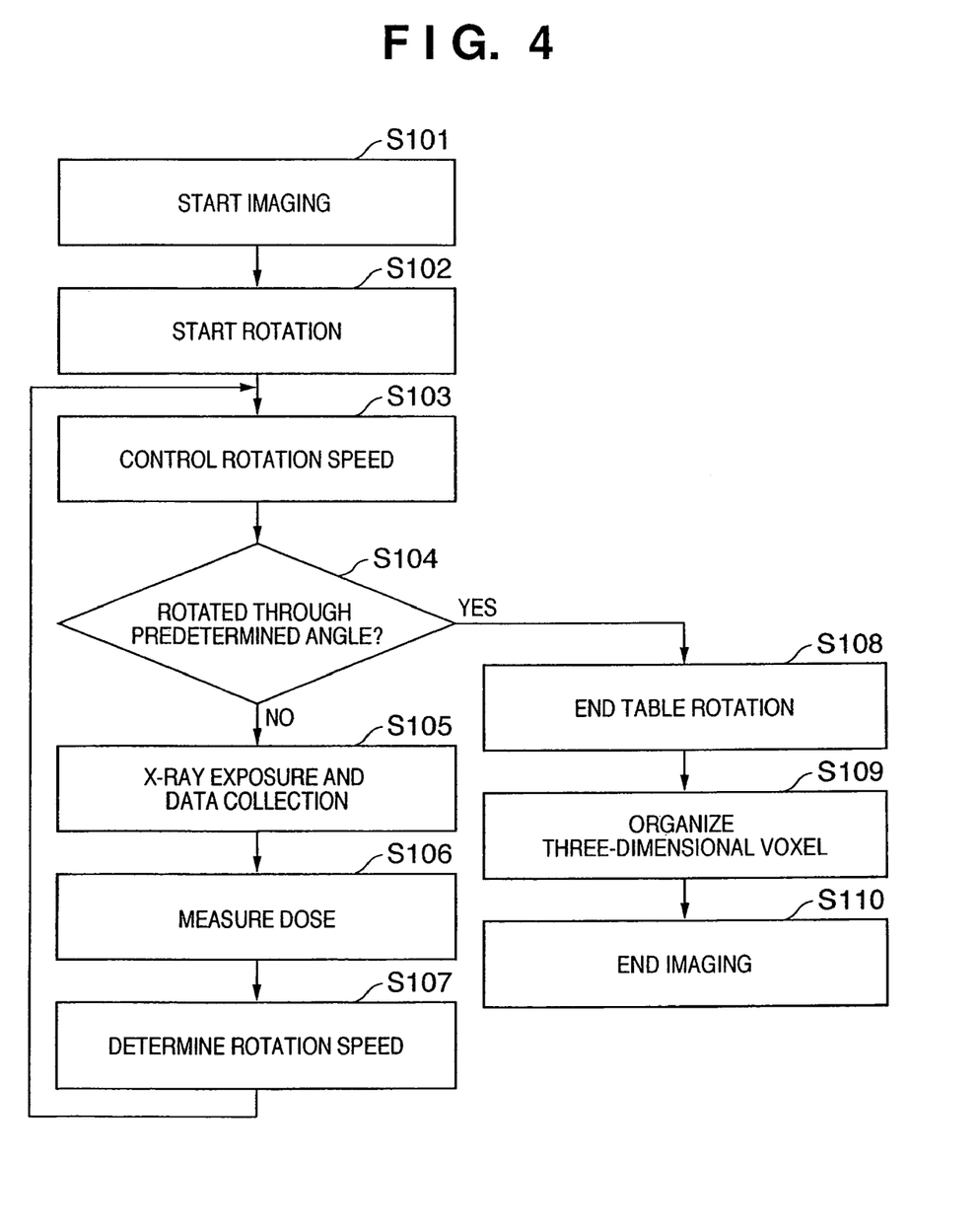
FIG. 4 is a flowchart showing a radiographic process according to the first embodiment.
Figure 5:
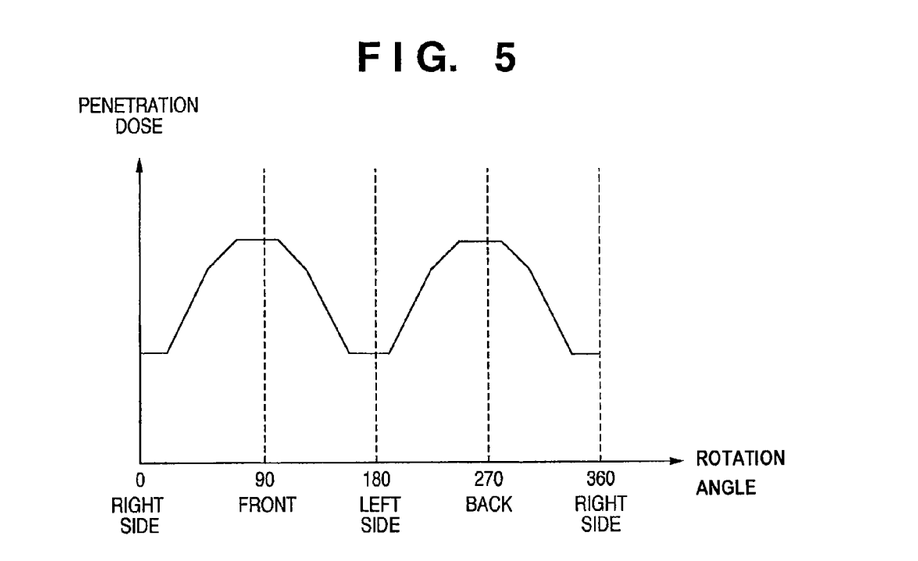
FIG. 5 is a diagram showing the relationship between rotation angle and penetration dose according to the first embodiment.
Figure 6:
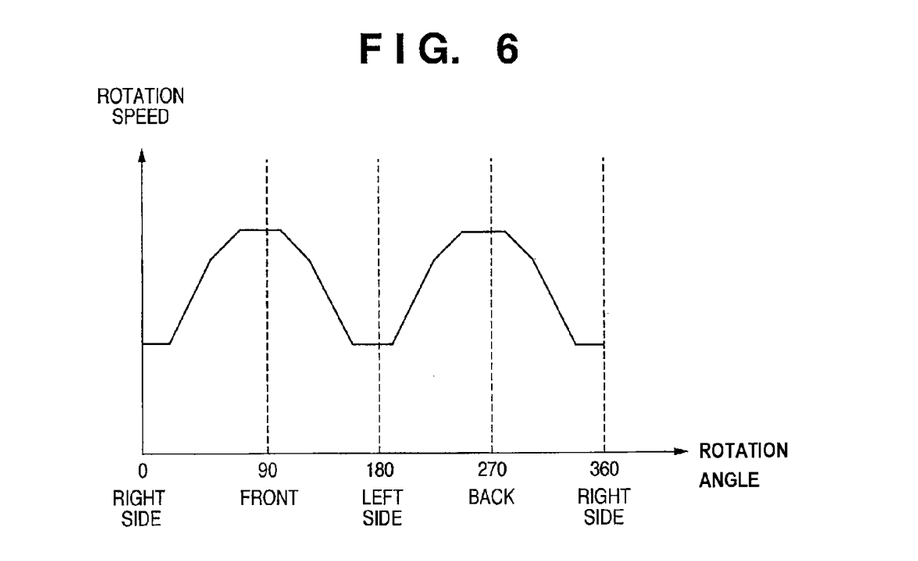
FIG. 6 is a diagram showing the relationship between rotation angle and rotation speed according to the first embodiment.

FIG. 1 is a block diagram showing the general organization of a radiographic device according to a first embodiment. FIG. 2 is a diagram illustrating an example of specific arrangement of the radiographic device according to the embodiment. FIG. 3 is a conceptual drawing illustrating a process executed by the radiographic device according to the embodiment. FIG. 4 is a flowchart showing the flow of a process according to the first embodiment. FIG. 5 is a diagram showing the dose of X ray radiation (X-ray reaching dose) having penetrated a region of interest and reached a two-dimensional X-ray sensor 12 while an X-ray source is emanating X ray radiation of a given dose and a rotation device 15 is rotating at a given rotation speed. In FIG. 5, the axis of ordinate indicates the dose of X-ray radiation having reached the two-dimensional X-ray sensor 12. The axis of abscissa indicates the rotation angle of the rotation device 15. In the example shown in FIG. 5, the following tendency is indicated. That is, the reaching dose is smaller for the side of the object (180° and 360°) and is larger for the front and back of the object (90° and 270°). FIG. 6 shows the relationship between the rotation angle and speed of a rotation table in the rotation device 15. The axis of ordinate indicates the rotation speed, while the axis of abscissa indicates the rotation angle. In this example, the rotation speed is smaller for the side of the object (180° and 360°) and is larger for the front and back of the object (90° and 270°). The radiographic device according to the first embodiment detects X-ray penetration dose during a radiographic operation and controls the rotation speed of the rotation table on the basis of the detected X-ray penetration dose. For example, if the X-ray penetration dose has such characteristics as shown in FIG. 5, such speed control as shown in FIG. 6 is executed.

In FIG. 1, reference numeral 11 denotes an X-ray generation device that emanates X rays 25 to an object 16. Reference numeral 15 denotes the rotation device including the rotation table that rotates with the object placed on it. Reference numeral 12 denotes a two-dimensional X-ray sensor which receives X rays having penetrated the object rotated on the rotation device 15 and which sequentially converts the X rays into an electric signal. The electric signal sequentially acquired is input to a data collection circuit 26. An A/D converter in the data collection circuit 26 then subjects the signals to A/D conversion to obtain image data, which is then supplied to a preprocess circuit 105. Note that, the A/D converter may be provided in the two-dimensional X-ray sensor 12.

The two-dimensional X-ray sensor 12 integrally integrates charges for a predetermined time and outputs the corresponding electric signal when the integration is finished. The electric signal is formed into image data. In other words, image data is generated for every combination of charge integration and discharge. In particular, an object rotating type radiographic device needs to sequentially acquire image data at every predetermined rotation angle and thus the reaching dose varies at every predetermined rotation angle (FIG. 5). Accordingly, the integration time thus needs to be controlled on the basis of the rotation angle.

The preprocess circuit 105 executes a preprocess such as an offset correction process, a gain correction process, or a LOG conversion on X-ray image data supplied by the data collection circuit 26. Reference numeral 14 denotes a generation circuit that generates (reconstructs) generation image data (also referred to as three-dimensional voxels) from a plurality of image data obtained at a plurality of rotation angles. The image data preprocessed by the preprocess circuit 105 is transferred to a main memory 20 and the generation circuit 14 via a CPU bus 24 under the control of a control circuit (CPU) 18. Generation image data (sometimes referred to as "tomogram image data" or "three-dimensional voxels") is thus generated. The generation circuit 14 uses, for example, a filter process or a back projection process to generate generation image data. Any method for generating generation image data may be used but it is common to use a Ramachandran or Shepp-Logan function for the filter process. Further, filtered image data is back projected. An example of an algorithm covering the filter process to the back projection is a Feldkamp's algorithm. However, the present invention is not limited to this. Once the back projection is completed to generate generation image data, a tomogram is displayed on a display 19 on the basis of the generation image data. Further, the generation image data generated is saved to the main memory 20.

A specific arrangement of the radiographic device will be described with reference to FIG. 2 showing the radiographic device of the present embodiment in a top and side views.

The X-ray generation device 11 emanates X rays of cone beams to the object. FIG. 2 shows the X-ray generation device 11 as the focus of the X rays. As shown in FIG. 2, the spread angle of the X rays in a vertical direction (body axis direction or Z direction) is called a cone angle. The spread of the X rays in a horizontal direction is called a fan angle. Further, the rotation device 15 has the rotation table that rotates with the object 16 placed on it; the object 16 is irradiated with X rays emanated by the X-ray generation device 11. This organization allows the object 16 to rotate in an X-ray irradiation region relative to the X rays. Further, reference numeral 103 denotes a chest support provided to fix the object 16. The chest support 103 is supported by a strut fixed to the rotation table.

The X rays emanated by the X-ray generation device 11 penetrate the object 16, chest support 103 and scattered radiation removal grids (not shown). The X-rays are then detected by the two-dimensional X-ray sensor 12, which converts the X rays into an electric signal. As described above, the two-dimensional X-ray sensor 12 integrally accumulates charges for a predetermined time and acquires an electric signal when the charge integration is finished. Image data is generated every time an electric signal is acquired. In other words, image data is generated every time charge integration is completed to acquire an electric signal. Furthermore, several types of methods are used to read an electric signal from the two-dimensional X-ray sensor 12. Typical methods for acquiring an electric signal are, for example, a destructive reading method of discharging integrated charges for each image data and a nondestructive reading method of integrating charges without discharging. The present embodiment may use any acquisition method. With any acquisition method, the time required to integrate changes required to acquire one image data is called a charge integration time. With the nondestructive reading method, the time for which charges are integrated between acquisition of one electric signal and acquisition of the next is called the charge integration time. Further, regardless of whether X rays are continuously or discontinuously emanated, the time for which charges are integrated in order to acquire one image data is called the charge integration time.

The present embodiment uses X rays. However, the present invention is not limited to X rays. The range of wavelength may be extended to radiation.

Now, with reference to FIGS. 1 and 3, description will be given of an imaging process executed by the radiographic device according to the present embodiment.

In FIG. 3, reference numeral 1 denotes image data obtained when the rotation table is at a certain rotation angle. The image data may be called a projection image. In the image data (projection image) 1, reference numeral 2 denotes a region of interest in the object. A penetration dose calculation circuit 17 calculates the average value 3 of the penetration dose in the region of interest 2 in the image data collected by the two-dimensional X-ray sensor 12. The region of interest is a predetermined region set on the two-dimensional X-ray sensor 12.

In general, a value for the image data is linearly proportional to the accumulated dose of X-ray radiation having reached the two-dimensional X-ray sensor 12. Accordingly, an average pixel value indicated by the average value 3 is a representative of the penetration dose in the region of interest 2. The average pixel value is also a representative of the dose of reached radiation having reached the predetermined region (corresponding to the region of interest 2) on the two-dimensional X-ray sensor 12. when the relationship between the accumulated dose of X-ray radiation having reached the two-dimensional X-ray sensor 12 and the value of the output signal is fixed, even if the relationship between the accumulated dose and the output signal is nonlinear, the value typical of the penetration dose in the region of interest 2 can be calculated from the value for the image data. Further, the region on the two-dimensional X-ray sensor to be defined as the region of interest 2 (area position and size) may be specified on an operation panel 21. If the object is a human body, it is appropriate that the region of interest 2 be a central part of the human body as shown in FIG. 3 because the dose decreases most sharply in the central part. Furthermore, the penetration dose may be based on the values of statistical amounts such as the maximum, minimum, and intermediate values instead of the average value of pixel values in the region of interest 2. Here, the control circuit 18 and penetration dose calculation circuit 17 calculate the X-ray penetration dose in the predetermined region of the two-dimensional X-ray sensor 12. Accordingly, the control circuit 18 and penetration dose calculation circuit 17 constitute a penetration dose measurement circuit (13).

The penetration dose measurement circuit 13 may be organized independently of the two-dimensional X-ray sensor 12. For example, the penetration dose measurement circuit 13 may comprise an X-ray sensor (not shown) and measure the dose of X-ray radiation having penetrated a predetermined region of the object, on the basis of an output from the X-ray sensor. Alternatively, a normal photo timer used for plain radiography may be used as the penetration dose measurement circuit 13.

Reference numeral 22 denotes a rotation speed calculation circuit that calculates a rotation speed to be set for the rotation device 15 on the basis of an output signal from penetration dose measurement circuit 13. For example, the rotation speed is calculated so as to be generally proportional to the average value 3 of the penetration dose in the region of interest 2. More specifically, the rotation speed may be obtained by dividing the average value 3 by a preset reference value 4 and multiplying the resulting value by a constant. For a large average value 3, the rotation speed is increased to reduce the dose of X-ray radiation reaching the two-dimensional X-ray sensor 12. That is to say, the rotation speed is controlled so as to decrease when the average value 3 is smaller than the reference value 4 and to increase when the average value 3 is larger than the reference value 4. Then, thus calculated rotation speed 5 is supplied to a table rotation speed control unit 6 of the rotation device 15 to control the rotation speed of the rotation table. Further, the present embodiment acquires image data at every predetermined rotation angle. For example, to acquire (take) 1,000 image data during a 360° rotation, charge integration and discharge is carried out so as to acquire one image data per 0.36°. Accordingly, the integration time for the two-dimensional X-ray sensor 12 varies depending on the rotation speed of the rotation table. Thus, an almost constant penetration dose can be obtained which is independent of the rotation angle. Specifically, the rotation speed and the integration time for the two-dimensional X-ray sensor 12 are sequentially determined on the basis of the rotation angle of the rotation device 15. The rotation speed and integration time are then controlled via the control circuit 18. Thus, the integration value of the dose of X-ray radiation having reached the two-dimensional X-ray sensor 12 during the integration time required to acquire one image data is controlled to be constant.

However, the penetration dose for the side of the object is normally half that for the front of the object. Consequently, the rotation speed may be reduced to half at the imaging angle of the side, that is, the rotation speed may become too low. Furthermore, the penetration dose at each angle may not need to be perfectly smoothened. In this case, the rotation speed may be obtained by multiplying a constant number to the amount of variation in penetration dose. Further, to control the SN ratio to within a predetermined range in order to deal with quantization noise in X rays, the square root of average value 3 of the penetration doses at the respective rotation angles may be compared with the reference value 4.

The penetration dose calculation circuit 17 and rotation speed calculation circuit 22 may be organized of software. In this case, the previously described functions are achieved by the control circuit 18 by executing supplied program codes.

In this radiographic device, the main memory 20 stores various data required for processing by the control circuit (CPU) 18 and includes a work memory used for operations by the control circuit 18. The control circuit 18 uses the main memory 20 to, for example, control the operation of the entire device in accordance with operations from the operation panel 21.

The radiographic device of the present embodiment is operated by the control of the control circuit 18 as described below.

An imaging start (S101) instruction is input via the operation panel 21. In accordance with an instruction from the control circuit 18, the rotation device 15 starts rotating the rotation table (S102 and S103). The control circuit 18 monitors an encoder signal (not shown) generated by the rotation device 15 to check whether the rotation table has reached a predetermined constant rotation speed and angle.

Once the predetermined rotation speed and angle are reached, the control circuit 18 sends a signal to the X-ray generation device 11 to start X-ray exposure. The control circuit 18 also collects image data via a correction circuit 106. The penetration dose calculation circuit 17 calculates the penetration dose of the region of interest 2 (S106). On the basis of the calculation of the penetration dose, the rotation speed calculation circuit 22 calculates and determines the rotation speed (5 in FIG. 3) (S107). The rotation speed is calculated by comparing the average value 3 with the preset reference value. The control circuit 18 and table rotation speed control unit 6 sequentially controls the rotation speed of the rotation device 15 (S103) on the basis of the determined rotation speed. The imaging process of steps S103 to S107 is continued until the rotation device 15 rotates through a predetermined rotation angle to allow a predetermined number of image data to be collected. Once the imaging process at each predetermined angle, that is, collection of required image data (7 in FIG. 3), is completed (S104), the rotation of the rotation device 15 is finished (S108) and generation image data (three-dimensional voxel 9 in FIG. 3) is generated (S109). The generation image data is then displayed to complete the imaging (S110).

As described above, the first embodiment determines the rotation speed and the integration time for the two-dimensional X-ray sensor at every rotation angle of the rotation device 15 on the basis of the dose of X-ray radiation having penetrated the object. This is effective in controllably making constant the integration value of the dose of X-ray radiation having reached the two-dimensional X-ray sensor 12 during the integration period required to image data at every rotation angle.

In other words, the first embodiment is effective in controllably making the penetration dose constant without allowing the output from the radiographic device to be externally varied. This eliminates the need to sequentially control the output from the radiographic device, thus enabling the simplification of control using a conventional X-ray generation device.

SECOND EMBODIMENT

Figure 7:
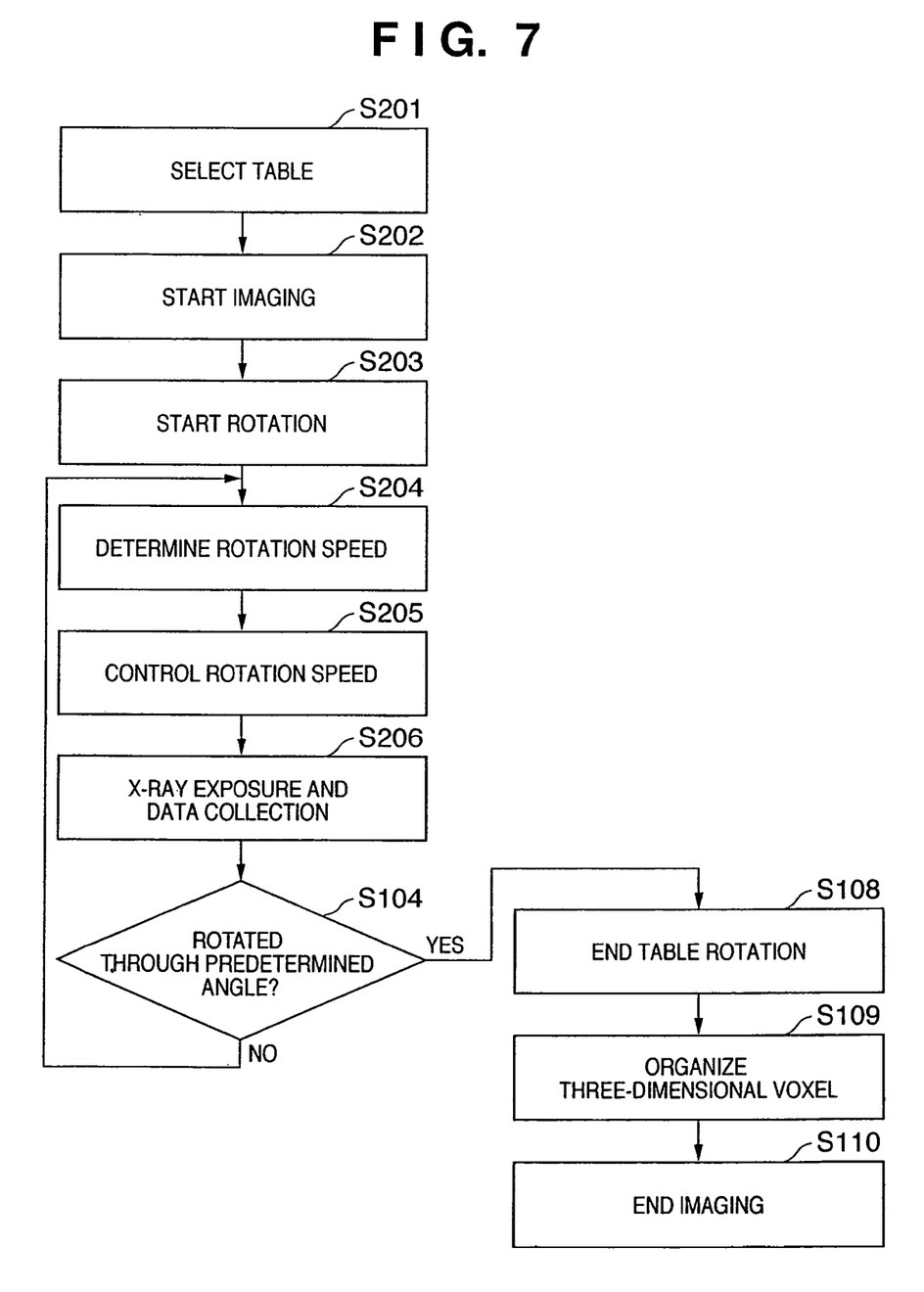
FIG. 7 is a flowchart showing a radiographic process according to a second embodiment.
Figure 8:
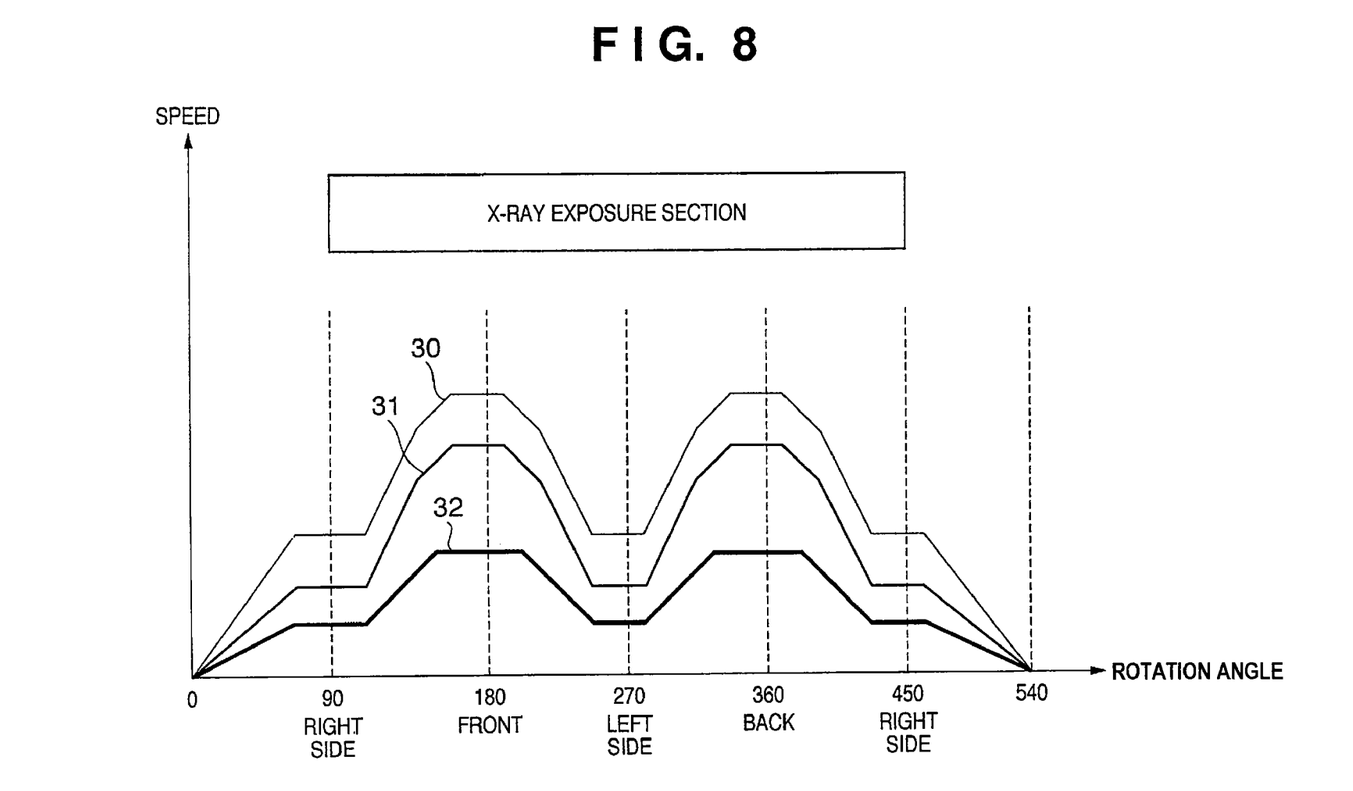
FIG. 8 is a diagram showing a table describing the relationship between rotation angle and rotation speed according to the second embodiment.

A second embodiment will be described with reference to FIGS. 7 and 8. FIG. 7 is a flowchart showing the flow of a radiographic process according to the second embodiment. FIG. 8 shows an example of a plurality of tables 30, 31, and 32 describing the relationship between the rotation angle and speed of the rotation device 15. The tables are stored in the main memory 20 in association with an body part such as the chest or abdomen, or the body part size of the object. For example, reference numeral 30 denotes a chest image of a small person, reference numeral 31 denotes a chest image of a big person, and reference numeral 32 denotes an example of a table for rotation speed control corresponding to abdominal imaging. Since the cross section of a human body is generally elliptical, the relationship between the rotation angle and the penetration dose of the region of interest can be generalized. This enables the tables to be generalized in association with the body part and/or body part size.

The organization of the radiographic device according to the second embodiment is similar to that according to the first embodiment (FIGS. 1 and 2) and its description is thus omitted. Also, in the summary of the imaging process shown in FIG. 3, the process of determining the rotation speed of the rotation table, denoted by reference numerals 3, 4, and 5, is replaced with the process of determining the rotation speed using the tables as shown in FIG. 7.

Now, the flow of the imaging process according to the second embodiment will be described with reference to the flowchart in FIG. 7.

One of the plurality of tables stored in the main memory 20 is selected in accordance with an operation input to the operation panel 21 (S201). An imaging start (S202) instruction is input via the operation panel 21. In accordance with an instruction from the control circuit 18, the rotation device 15 starts rotating the rotation table (S203 to S205). The control circuit 18 monitors an encoder signal (not shown) generated by the rotation device 15 to check whether the rotation table has reached a predetermined constant rotation speed and angle. Once the predetermined rotation speed and angle are reached, the control circuit 18 sends a signal to the X-ray generation device 11 to start X-ray exposure. The processing from step S204 to step S206 is repeated to collect image data at every predetermined angle until the rotation table rotates through a predetermined rotation angle (for example, in FIG. 8, 540°). More specifically, in accordance with the selected table, the control circuit 18 determines the rotation speed and integration time (time required to acquire one image data) at every rotation angle of the rotation table in the rotation device 15 (S204). In accordance with the determined rotation speed, the rotation speed and integration time are sequentially controlled at every rotation angle of the rotation device 15 (S205). An imaging process is executed to collect image data (S206).

In the example shown in FIG. 8, the rotation starts from the back position (0°), and the rotation speed becomes constant at the side position where the rotation angle is 90°. X-ray exposure is then started. As projection angle advances toward the front, the rotation speed of the rotation table increases. The rotation speed reaches the maximum value in the front position where the rotation angle is 180°. However, the upper limit of the maximum rotation speed corresponds to the maximum frame rate of the two-dimensional X-ray sensor 12.

Imaging is continued until the rotation table of the rotation device 15 rotates through a predetermined rotation angle (for example, in FIG. 8, 540°) to allow a predetermined number of image data to be collected (however, imaging is carried out between 90 and 450°). Once collection of image data taken at every predetermined angle is completed (S104), the rotation of the rotation device 15 is finished (S108) and generation image data (three-dimensional voxel 9) is generated (S109). The generation image data is then displayed to complete the imaging (S110).

As described above, the second embodiment determines the rotation speed and the integration time for the two-dimensional sensor for every rotation angle of the rotation device 15 on the basis of tables in which the relationship between the rotation angle and speed as shown in FIG. 8 is pre-registered. This controllably makes constant the integration value of the dose of X-ray radiation having reached the two-dimensional X-ray sensor 12 during the integration period required to image data at every rotation angle. Accordingly, the penetration dose measurement circuit and the like shown in the first embodiment can be eliminated. The second embodiment can thus effectively control the penetration dose of X ray radiation using an organization simpler than that of the first embodiment.

Further, like the first embodiment, the second embodiment can effectively control the penetration dose during imaging to a fixed value even if the output from the radiographic device cannot be externally controlled, that is, the output remains fixed. This eliminates the need to sequentially control the output from the radiographic device. Thus, an object rotating type radiographic device can be effectively implemented by using a conventional X-ray generation device and setting X-ray generation timings.

THIRD EMBODIMENT

Figure 9:
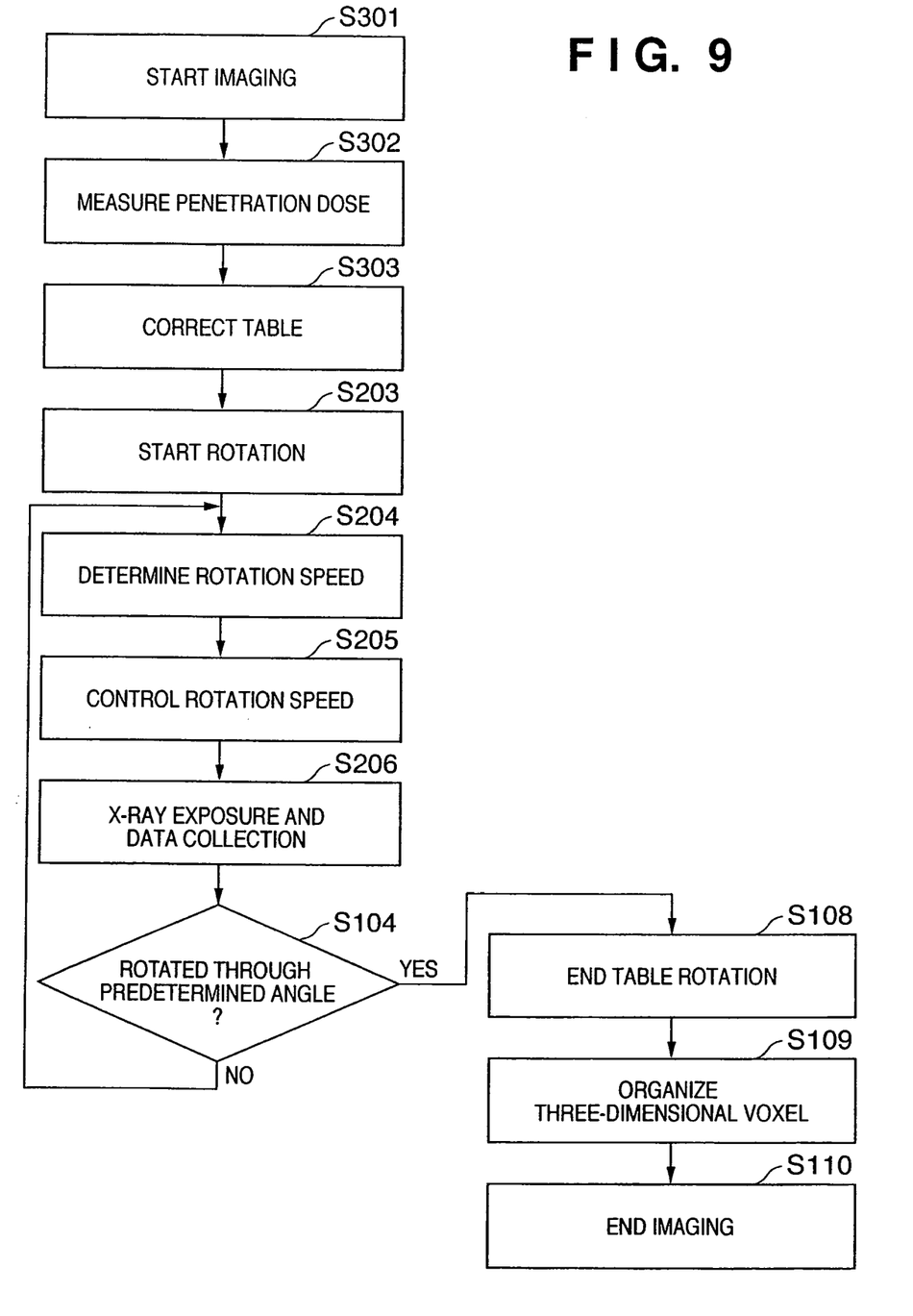
FIG. 9 is a flowchart showing a radiographic process according to a third embodiment.
Figure 10:
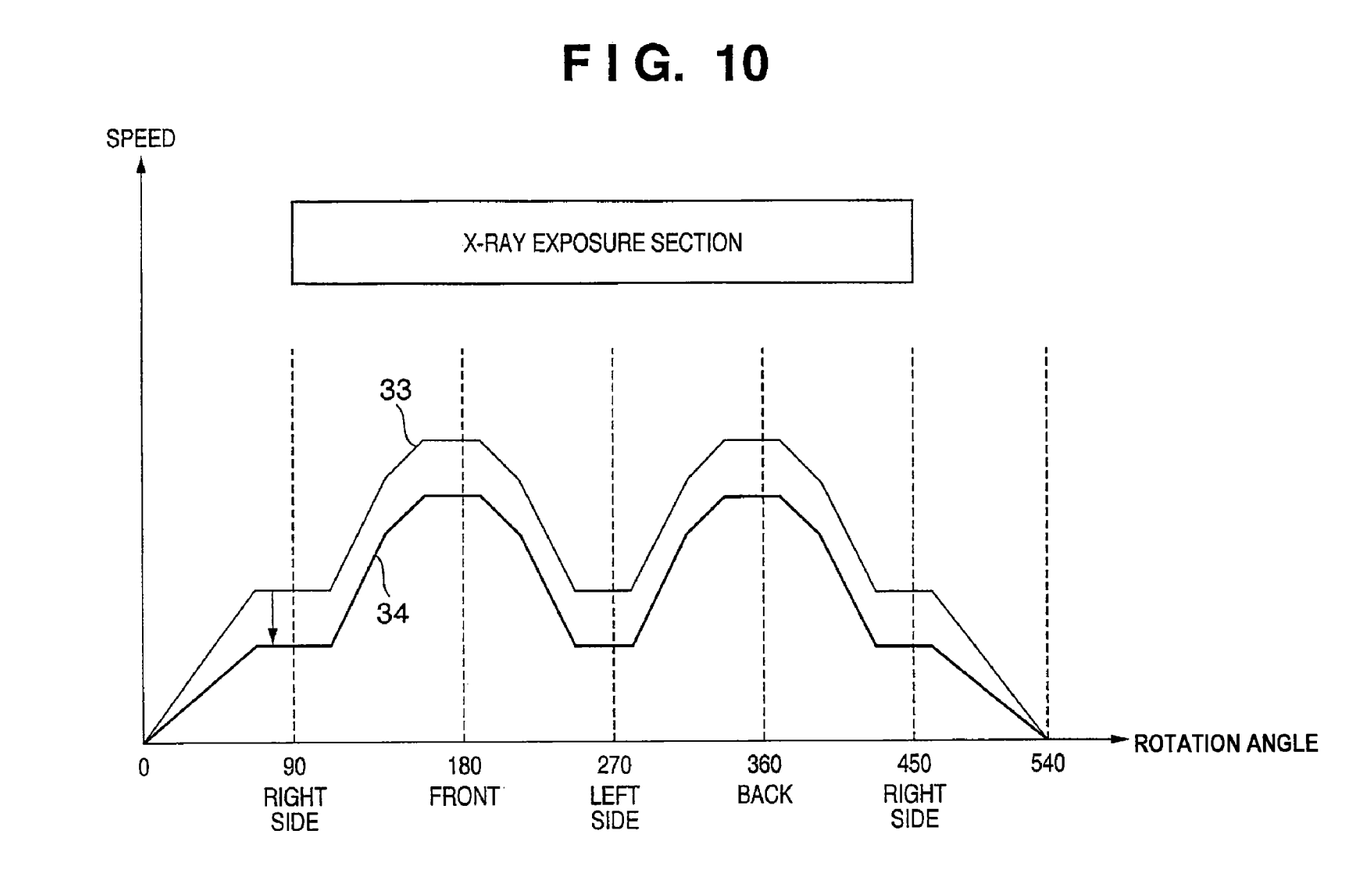
FIG. 10 is a diagram showing a table describing the relationship between rotation angle and rotation speed according to the third embodiment.

A third embodiment will be described with reference to FIGS. 9 and 10. FIG. 9 is a flowchart showing the flow of a radiographic process according to a third embodiment. FIG. 10 is a diagram showing a table 33 describing the relationship between the rotation angle and speed of the rotation device 15 and a corrected table 34 according to the third embodiment. The tables shown in FIG. 10 are stored in the main memory 20.

The organization of the radiographic device according to the third embodiment is similar to that according to the first embodiment (FIGS. 1 and 2) and its description is thus omitted. In the summary of the imaging process shown in FIG. 3, the process of determining the rotation speed of the rotation table, denoted by reference numerals 3, 4, and 5, is replaced with the process of determining the rotation speed using the corrected table as shown in FIG. 10.

Now, the process of the third embodiment will be described with reference to the flowchart in FIG. 9.

An imaging start (S301) instruction is input via the operation panel 21. In accordance with an instruction from the control circuit 18, pre-scan is carried out on the object over a predetermined rotation range (S302). For example, the pre-scan is carried out while the rotation table in the rotation device 15 rotates from 90 to 180°. The penetration dose measurement circuit 13 measures the dose of X-ray radiation having penetrated the object and stores it in the main memory 20. The X-ray dose in the pre-scan is smaller than that in the main scan. Even during the pre-scan, the penetration dose in the region of interest set in the two-dimensional X-ray sensor 12 is measured as described in the first embodiment.

The control circuit 18 corrects the table 34 on the basis of the measurements stored in the main memory 20 (S303). For example, the table is corrected on the basis of the ratio of the average value of the measurements to a preset reference value (for example, the table 34 is multiplied by the reference value/average value).

The control circuit 18 then starts rotating the rotation table to begin the main scan (S203). The rotation table may continue rotating between the pre-scan and main scan. The control circuit 18 monitors an encoder signal (not shown) generated by the rotation device 15 to check whether the rotation table has reached a predetermined constant rotation speed and angle. Once the predetermined rotation speed and angle are reached, the control circuit 18 sends a signal to the X-ray generation device 11 to start X-ray exposure. The processing from step S204 to step S206 is repeated to collect image data at every predetermined angle until the rotation table rotates through a predetermined rotation angle (for example, in FIG. 10, 540°). More specifically, in accordance with the table corrected in S303, the control circuit 18 determines the rotation speed and integration time (time required to acquire one image data) at every rotation angle of the rotation table in the rotation device 15 (S204). In accordance with the determined rotation speed, the rotation speed and integration time are sequentially controlled at every rotation angle of the rotation device 15 (S205). An imaging process is executed to collect image data (S206).

In the example shown in FIG. 10, the rotation starts from the back position (0°), and the rotation speed becomes constant at the side position where the rotation angle is 90°. X-ray exposure is then started. As projection angle advances toward the front, the rotation speed of the rotation table increases. The rotation speed reaches the maximum value at a front position where the rotation angle is 180°. However, the upper limit of the maximum rotation speed corresponds to the maximum frame rate of the two-dimensional X-ray sensor 12.

Imaging is continued until the rotation table of the rotation device 15 rotates through a predetermined rotation angle (for example, in FIG. 10, 540°) to allow a predetermined number of image data to be collected (however, imaging is carried out between 90 and 450°). Once collection of image data taken at every predetermined angle is completed (S104), the rotation of the rotation device 15 is finished (S108) and generation image data (three-dimensional voxel 9) is generated (S109). The generation image data is then displayed to complete the imaging (S110).

As described above, by correcting the table on the basis of the measurements, the third embodiment can effectively control the penetration dose to a given value more accurately than the second embodiment in spite of differences among objects.

FOURTH EMBODIMENT

Description will be given of a fourth embodiment involving data collection for an offset and gain corrections executed by the correction circuit 106 as well as a process for data collection. The offset correction is processing executed for each pixel of image data. The offset is a phenomenon in which charges are integration for each pixel even without incidence of light attributed to X rays. The charge amount depends on the integration time. Thus, the value of the charge amount generally increases with time. However, the charge amount does not increase linearly with integration time, so that it is generally difficult to predict the offset value. Thus, if the integration time during imaging involving X-ray exposure is known, then before imaging, the same integration time as that for the main scan is used to collect and correct the offset amount for each pixel.

Figure 11:
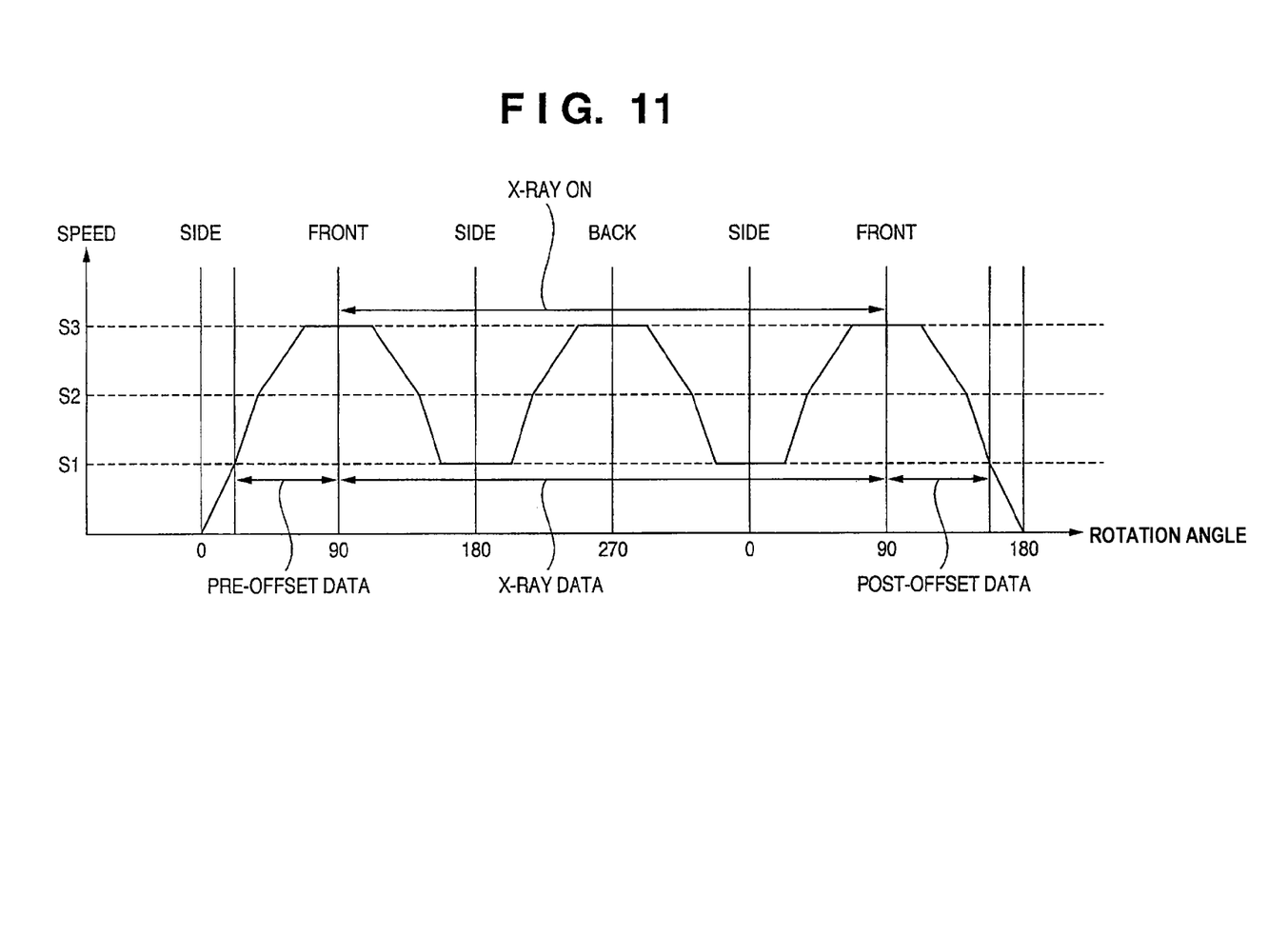
FIG. 11 is a diagram showing the relationship between rotation angle and offset data according to a fourth embodiment.

However, if the rotation speed of the rotation device 15 is varied for imaging, offset data is required for each image data. In FIG. 11, the axis of abscissa indicates the rotation angle of the rotation table in the rotation device 15, while the axis of ordinate indicates the rotation speed. First, the human body is installed in the device so that the rotation starts from the side of the human body. For example, the rotation angle at this position is 0°. Pre-offset data starts to be collected when the rotation speed of the rotation table reaches S1. The pre-offset data is continuously collected until the speed exceeds S2 and reaches S3, and X rays are located so as to enter the front of the human body (rotation angle: 90°). In this case, the pre-offset data is collected at an every constant rotation angle corresponding to the timing for acquiring image data.

The pre-offset data is saved to the main memory 20. When the X rays are located so as to enter the front of the human body (rotation angle: 90°), X-ray exposure is started to allow X-ray data to be collected. FIG. 11 shows the case of full scan in which X-ray exposure is carried out while the rotation device 15 rotates through 360°. During the rotation, the rotation speed of the rotation device 15 varies from S3 to S1.

After the rotation through 360°, the X-ray exposure is stopped and post-offset data is collected until the speed becomes S1. Now, description will be given of how to use the pre- and post-offset data in the offset process. The pre-offset data is often different from the post-offset data even with the same integration time. This is expected to be due to the temperature characteristics of the two-dimensional X-ray sensor 12. Thus, the offset data can be utilized in the following two ways.

The pre- and post-offset data are averaged for each corresponding integration time, and The pre-offset data is applied to the former half (from 90° to 270°) of the X-ray data, whereas the post-offset data is applied to the latter half (from 270° to 90°) of the X-ray data.

In either case, the offset process is executed by subtracting, from image data, offset data collected during the same integration time for which the image data has been collected.

The fourth embodiment uses encoder pulses output by the rotation table to collect offset data for every given number of encoder pulses. To collect projection data in 1,000 directions during rotation through 360°, image data is collected every time the rotation table rotates through 0.36°. Accordingly, offset data is collected at every rotation angle of 0.36° in association with the integration time for the imaging process for each image data. In a section in which the speed of the rotation table 15 varies, strictly speaking, the integration time varies at every rotation angle of 0.36°. However, the offset value may not reflect a small change in integration time. For example, the speed S1 is assumed to be equal to 8 seconds per rotation, and the speed S3 is assumed to be equal to 5 seconds per rotation. Rotation through 0.36° requires 8 msec at the speed S1 and 5 msec at the speed S3 (these times correspond to integration times). If the section between the speeds S1 and S3 is divided into 250 integration sections, the difference in integration time between the adjacent sections is about 0.01 msec, which corresponds to a very small change. Thus, N data collected during consecutively varying integration times may be averaged so that the average value can be used to correct the offset in the X-ray data collected during the integration times corresponding to the averaging section. The averaging enables a variation in offset data to be corrected.

The method for collecting offset data has been described. However, the above description also applies to gain data. With the imaging region filled only with air, the gain data is periodically (for example, once per several months) acquired before scanning of the object. It is known that an error in the correction of the gain data can be minimized by approximation to the dose of X-ray radiation at the time of imaging of the object. Accordingly, since a variation in the rotation speed of the rotation device 15 varies the dose of X rays irradiated, the gain data is desirably acquired with the rotation speed varied. This also applies to all the above tables, and the gain data can be collected by imaging only air using the corresponding table.

As described above, by preparing the correction data corresponding to the rotation angle of the rotation device, the fourth embodiment can effectively achieve accurate corrections.

The above embodiments show examples of full scan. However, of course, the present invention is also applicable to half scan. The above embodiments also show an example of a radiographic device of the type that rotates an object. However, it is apparent to those skilled in the art that the imaging control of the present invention is applicable to the case where X-ray image data is collected using a radiographic device rotating an X-ray sensor and an X-ray generation device with the object fixed.

The scope of the present invention includes the following aspect. Program codes for realizing the functions of the above embodiments (for example, the functions realized in accordance with the flowcharts in FIGS. 4, 7, and 9) are supplied to a computer in an apparatus or system connected to various devices so as to operate the devices to achieve the functions of the above embodiments. The various devices are then operated in accordance with programs stored in the computer (CPU or MPU) in the system or apparatus.

Further, in this case, the program codes themselves in the software achieve the functions of the above embodiments. The present invention is generated by the program codes themselves and means for supplying the program codes, for example, storage media in which the program codes are stored.

Examples of the storage media in which the program codes are stored include a floppy disk, a hard disk, an optical disk, a magneto optic disk, a CD-ROM, a magnetic tape, a nonvolatile memory card, and a ROM.

Of course, the program codes are also included in the embodiments of the present invention not only if the computer executes the program codes to achieve the functions of the above embodiments but also if the program codes cooperate with an OS (Operating System), another application software, or the like in achieving the functions of the above embodiments.

Of course, the program codes are also included in the present invention if the supplied program codes are stored in a memory provided in an expanded board in the computer or in an expanded unit connected to the computer, so that on the basis of instructions in the program codes, a CPU or the like provided in the expanded board or unit executes a part or all of the actual process to achieve the functions of the above embodiments.

It will be appreciated that since various embodiments of the present invention can clearly be broadly devised without departing from the spirit or scope of the present invention, the present invention is not limited to the above particular embodiments unless specified in the accompanying claims.

CLAIM OF PRIORITY

This application claims the benefit of Japanese Application No. 2004-013835, filed Jan. 22, 2004, which is hereby incorporated by reference herein in its entirety.

The invention claimed is:

1. A radiographic device comprising:
   an X-ray generation unit adapted to generate X rays;
   a rotation unit having a rotation mechanism that relatively rotates an object in a region irradiated with the X rays;
   an X-ray sensor that executes a plurality of imaging processes using X rays having penetrated the object while the object is being rotated by said rotation unit, to acquire a plurality of first image data; and
   a memory storing a table describing a relationship between a rotation angle and speed of the rotation mechanism,
   wherein said rotation unit is configured to control a rotation speed of the rotation mechanism, on the basis of the table, such that the X rays reaching the X-ray sensor during a charge accumulation time in each of the plurality of imaging processes have a fixed integration value during rotation of the rotation mechanism.

2. The radiographic device according to claim 1, wherein:
   said memory stores a plurality of tables describing a relationship between a rotation angle and speed of the rotation mechanism,
   the radiographic device further comprises a selection unit adapted to select one of the plurality of tables to be utilized, and
   said rotation unit rotates the rotation mechanism in accordance with the table selected by said selection unit.

3. The radiographic device according to claim 2, wherein said selection unit selects the table on the basis of a site of the object and/or a physique of the object.

4. The radiographic device according to claim 1, further comprising:
   a penetration dose measurement unit adapted to measure the penetration dose of the X ray radiation having penetrated the object; and
   a correction unit adapted to correct a value in the table on the basis of the penetration dose, and
   wherein said rotation unit controls rotation speed of the rotation mechanism in accordance with the table corrected by said correction unit.

5. The radiographic device according to claim 1, further comprising a correction unit adapted to correct the first image data on the basis of correction data for correcting an output from the X-ray sensor in association with a rotation angle of the rotation mechanism.

6. The radiographic device according to claim 5, wherein the correction data is image data used for offset correction or gain correction.

7. The radiographic device according to claim 1, further comprising a change unit adapted to change the charge accumulation time for the X-ray sensor depending on a rotation angle of the rotation mechanism.

8. The radiographic device according to claim 1, further comprising a generation device that generates second image data on the basis of the plurality of first image data.

9. A radiographic method comprising:
   an X-ray generation step of generating X rays from an X-ray generation unit;

a rotation step of rotating a rotation mechanism that relatively rotates an object in a region irradiated with the X rays;

an imaging step of executing a plurality of imaging processes using the X rays having penetrated the object during rotation of the object by the rotation step, to acquire a plurality of first image data; and an image generating step of generating an image from the first image data, wherein, in the rotation step, a rotation speed of the rotation mechanism is controlled on the basis of a table stored in a memory, that describes a relationship between a rotation angle and speed of the rotation mechanism, such that a rotation speed of the rotation mechanism is controlled so that the X rays reaching the X-ray sensor during a charge accumulation time in each of the plurality of imaging processes have a fixed integration value during rotation of the rotation mechanism.

* * * * *